(12) United States Patent
Nakamura et al.

(10) Patent No.: US 6,186,023 B1
(45) Date of Patent: Feb. 13, 2001

(54) AUTOMATIC BALANCING APPARATUS FOR BALANCING STAND

(75) Inventors: Katsushige Nakamura; Masao Doi, both of Tokyo (JP)

(73) Assignee: Mitaka Kohki Co., Ltd., Tokyo (JP)

( * ) Notice: Under 35 U.S.C. 154(b), the term of this patent shall be extended for 0 days.

(21) Appl. No.: 09/362,688

(22) Filed: Jul. 29, 1999

(30) Foreign Application Priority Data

Nov. 5, 1998 (JP) .................................................. 10-314880

(51) Int. Cl.[7] .............................. B25J 17/00; B25J 19/00; A47F 5/00; G01C 15/10; G08B 21/00
(52) U.S. Cl. ...................... 74/490.01; 248/123.2; 33/366; 340/689; 901/48; 901/49
(58) Field of Search ............................. 74/490.01; 16/400; 414/917; 901/48, 49; 33/333, 365, 366.11, 366.24, 366.27; 340/689, 686; 248/123.2

(56) References Cited

U.S. PATENT DOCUMENTS

| | | |
|---|---|---|
| 2,156,862 | 5/1939 | Maugard . |
| 3,805,398 * | 4/1974 | Russell et al. ...................... 33/366 X |
| 4,484,186 * | 11/1984 | Wood et al. .......................... 340/389 |
| 4,571,844 * | 2/1986 | Komasaku et al. ..................... 33/366 |
| 5,332,181 * | 7/1994 | Schweizer et al. ............... 248/123.1 |
| 5,480,114 | 1/1996 | Nakamura . |
| 5,577,414 * | 11/1996 | Ogawa et al. ..................... 74/490.03 |
| 5,667,186 | 9/1997 | Luber et al. . |
| 5,713,545 | 2/1998 | Nakamura . |
| 6,045,104 * | 4/2000 | Nakamura et al. ........... 248/123.2 X |
| 6,105,909 * | 8/2000 | Wirth et al. ....................... 248/123.2 |

OTHER PUBLICATIONS

Patent Abstracts of Japan, Nakamura Masakazu, Medical Stand Device, Oct. 13, 1998.

* cited by examiner

Primary Examiner—Charles A. Marmor
Assistant Examiner—Roger Pang
(74) Attorney, Agent, or Firm—Arent Fox Kintner Plotkin & Kahn, PLLC

(57) ABSTRACT

According to the invention, a latch 17 provided at a distal end of a lever 16 is urged to engage with a gear 13 fixed at a joint fulcrum 2 jointing a vertical arm 1 and a horizontal arm 3, for effecting angular displacement, thereby actuating a switch 20a,20b for a detecting mechanism. Because the mechanism is compact, it is easily applicable to existing balancing stands in which for example a parallel linkage mechanism formed with a combination of a plurality of vertical arms and horizontal arms is supported at a predetermined fulcrum.

4 Claims, 2 Drawing Sheets

AUTOMATIC BALANCING APPARATUS FOR BALANCING STAND

BACKGROUND OF THE INVENTION

1. Field of the Invention

The present invention relates to an automatic balancing apparatus for a balancing stand, which suspends and supports weights.

2. Description of the Prior Art

There conventionally exist balancing stands which suspend and support weights in optional positions in the air. For example, balancing stands capable of holding weights such as an operation microscope and auxiliary devices are used in the medical field (e.g. an Official Gazette of Japanese Patent Application Laid-open (kokai) No. 269463-1994). Balancing stands of the type generally have a structure in which a parallel linkage mechanism formed by a combination of a plurality of vertical arms and horizontal arms is supported at a predetermined fulcrum, an operation microscope and/or auxiliary devices is/are held at one end of the parallel linkage mechanism, and a counterweight is provided at the other end of the mechanism for balancing the weight relative to the operation microscope, etc.

A location of the balancing stand is selected to an optimum position according to the content of the operation to be performed, and balance adjustment is effected there. Since the auxiliary devices such as a side scope for an assistant doctor and a video camera are secured to the operation microscope, adjustment of whole balance is made by displacing the positions of the counterweight manually in accordance with the weight of the auxiliary devices.

However, positional adjustment of a counterweight has been made manually in a structural sense in the earlier technologies, so that balancing adjustment has not been effected so promptly. Further, since the parallel linkage mechanism moves to a large degree in unbalanced conditions, there is a possibility that the linkage mechanism may strike against some apparatus or the like present nearby. Under the circumstances, proposals of automatic balancing apparatuses applicable to the balancing stand of this kind have been waited. More specifically, proposals of automatic balancing apparatuses having a compact structure and applicable to the conventional balancing stands have been especially waited.

The present invention was accomplished in view of the earlier technologies, and its object is to provide an automatic balancing apparatus having a compact structure, capable of adjusting balance in an automatic and essentially prompt manner, and preventing arms from moving so substantially in unbalanced conditions.

SUMMARY OF THE INVENTION

In order to achieve the above object, an automatic balancing apparatus for a balancing stand according to the present invention is comprised of: a vertical arm and a horizontal arm mounted to a joint fulcrum in a pivotal manner and the joint fulcrum is fixed to either the vertical arm or a horizontal arm; weights being weighed to an end side of the horizontal arm; a counterweight for balancing with respect to the weights being weighed to the other end side; a detecting mechanism for detecting unbalanced conditions of the horizontal arm; and a driving mechanism for displacing the counterweight in a balancing direction in response to signals outputted by the detecting mechanism, and the detecting mechanism is provided with: a gear fixed to the joint fulcrum; a lever pivotally supported at a middle portion thereof on the vertical arm or horizontal arm whichever not being integrally fixed to the gear and the lever is further provided with at one end thereof a telescopic latch engageable with and detachable from the gear; a pair of stoppers opposed to each other with a predetermined clearance with the other end of the lever being sandwiched between the stoppers; urging means for holding the other end of the lever at a neutral position of the clearance; and a pair of switches provided opposed each other with the other end of the lever interposed therebetween and the switches is pushed by the other end of the lever.

In another invention, the automatic balancing apparatus for a balancing stand may be provided with a configuration in which a parallel linkage mechanism formed with a combination of a plurality of vertical arms and horizontal arms is supported at a predetermined fulcrum, and a detecting mechanism is provided on a joint fulcrum on which mounted are a set of a vertical arm and a horizontal arm of the parallel linkage mechanism.

According to the invention, a latch provided at a distal end of a lever is urged to engage with a gear fixed at a joint fulcrum jointing a vertical arm and a horizontal arm, for effecting angular displacement, thereby actuating a switch for a detecting mechanism. Because the mechanism is compact, it is easily applicable to existing balancing stands in which for example a parallel linkage mechanism formed with a combination of a plurality of vertical arms and horizontal arms is supported at a predetermined fulcrum. Signals are transmitted from the actuated switch to a driving mechanism to move the counterweight automatically in a balancing direction for effecting balancing adjustment, so that time as required for an adjustment operation can be reduced and unskilled operators can perform an adjustment operation easily. The detecting mechanism is further provided with a pair of stoppers combined with a lever for preventing the horizontal arm and a parallel linkage mechanism interlocking therewith from moving so substantially beyond abutment of the stoppers against the lever in unbalanced conditions, thereby there is no danger that the horizontal arm may strike against persons or equipment present nearby. Thus, physical engagement between the stoppers and the other end of the lever forcedly prevents the horizontal arm from rotating further in a structural sense. Accordingly, if an electrical failure should happen to the switches or the like, any substantial movement of the horizontal arm caused by unbalance in weight will be completely prevented and with the result of that, the present apparatus is advantageous in an aspect of safety.

The present invention is not limited to the above description, and other objects, advantages, features and uses of the invention will be apparent from the following description taken in conjunction with the accompanying drawings, and it is to be understood any appropriate changes and modifications made without departing from the spirit or scope of the invention fall within the scope of the invention.

DESCRIPTION OF THE PREFERRED EMBODIMENTS

Preferred embodiments of the invention are now being described with reference to the drawings. For purpose of description, it is assumed "A" denotes frontward and "B" denotes backward.

Figure 1:
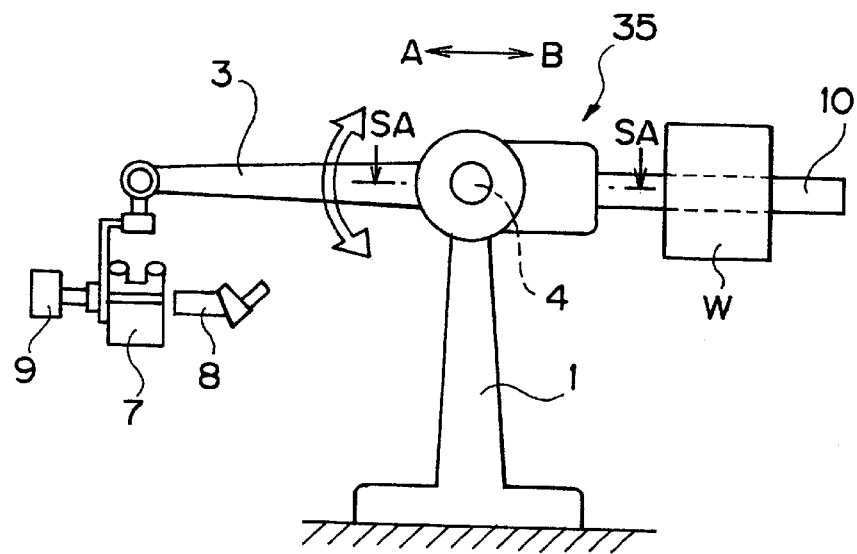
FIG. 1 is a schematic view illustrating a balancing stand according to a first embodiment of the invention.
Figure 2:
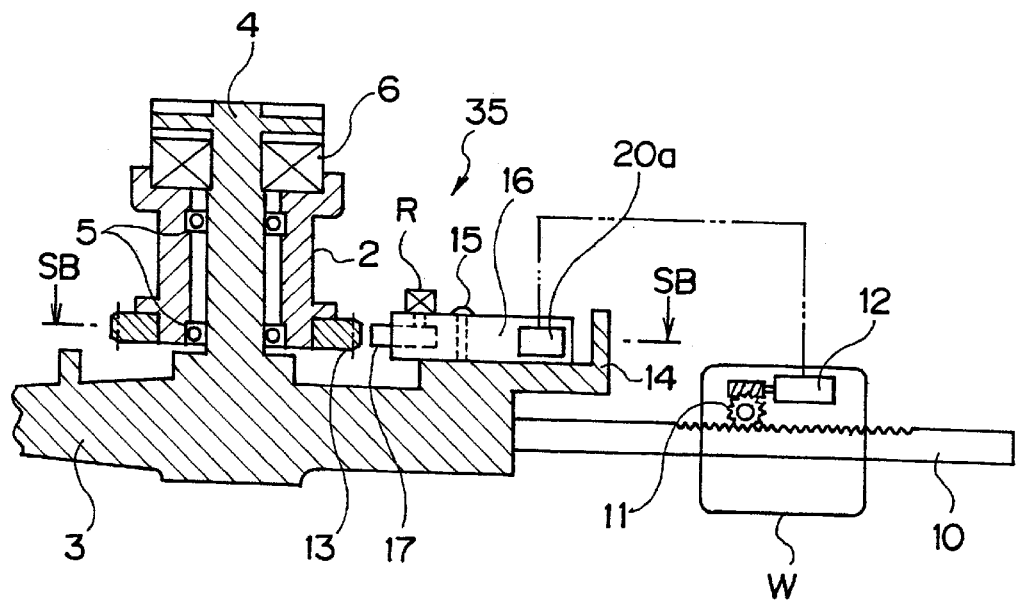
FIG. 2 is a cross-sectional view taken along line SA—SA in FIG. 1.
Figure 3:
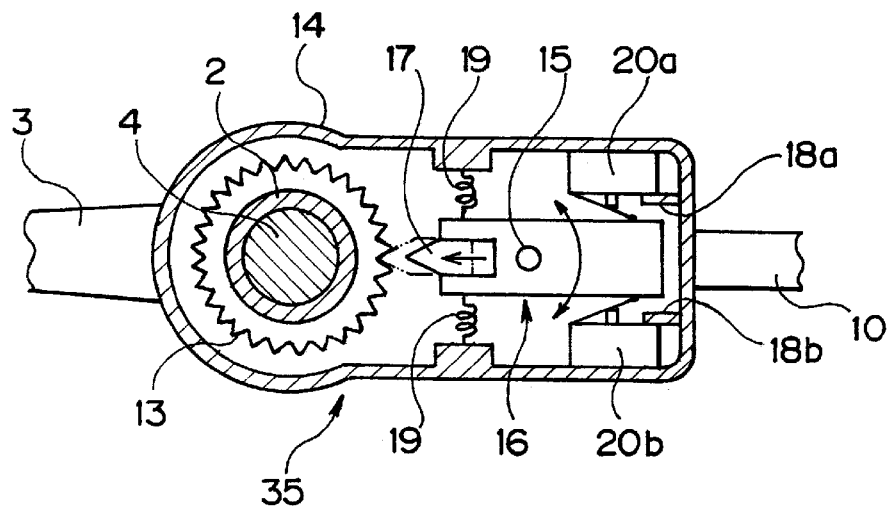
FIG. 3 is a cross-sectional view taken along line SB—SB in FIG. 2.

FIGS. 1 to 3 illustrate a balancing stand according to a first embodiment of the invention. Reference numeral 1 denotes a vertical arm which is fixed on a floor. A cylindrical joint fulcrum 2 is integrally formed at an upper end of the vertical arm 1, and a joint shaft 4 formed at an intermediate area of a horizontal arm 3 is inserted into the joint fulcrum 2 via a bearing 5. At an end of the joint fulcrum 2, an electromagnetic clutch 6 is provided so as to hold the connecting shaft against rotation. The electromagnetic clutch 6 is normally locked, but released when operated. Therefore, such a locked condition is maintained even in the event of a power failure and at an initial stage of setting the apparatus.

At a front end of the horizontal arm 3, "weights" i.e. an operation microscope 7, a side scope 8, and a camera 9 are supported in a suspended manner. The side scope 8 and a camera 9 are detachably mounted with respect to the operation microscope 7, and when the articles are detached, the weight of the "weights" will fluctuate.

At a rear end of the horizontal arm 3, a rack 10 on which rack teeth are provided longitudinally thereof is formed, and a counterweight W moveable along the rack 10 is provided. Within the counterweight W, a pinion 11 meshing on the rack 10 and a motor 12 rotating the pinion are provided. The rack 10, pinion 11 and motor 12 form a "driving mechanism" for moving the counterweight W.

Further, at an end of the cylindrical joint fulcrum 2 formed at the upper end of the vertical arm 1, a gear 13 is fixed. On the periphery of the joint shaft 4 of the horizontal arm 3, a flange which defines a case 14 is formed. Within the case 14, a detecting mechanism 35 is provided.

In particular, a lever 16 rotatably supported about a hinge 15 located on a horizontal arm 3 is provided in the case 14. The lever 16 is provided at a front end thereof with a retractable latch 17 which is engageable with and detachable from the gear 13. A reference symbol R in FIG. 2 denotes a solenoid which acts for extending and retracting the latch 17. Also provided in the case 14 is a pair of stoppers 18a,18b opposed with each other with a predetermined clearance and sandwiching a rear end of the lever 16 therebetween. Provided above and below the front end of the lever 16 is respectively a spring 19 as an "surging means" for holding the rear end of the lever 16 at a neutral position of the clearance. Provided above and below the rear end of the lever 16 are a pair of switches 20a,20b which are adapted to be pushed by the rear end of the lever 16. The switches 20a,20b and the motor 12 of the counterweight W are electrically connected with each other, and signals outputted by the switches 20a,20b determine both the direction and time of rotation.

As described above, the gear 13, lever 16, stoppers 18a,18b, spring 19 and switches 20a,20b the detecting mechanism 35. Thanks to the compact structure, the detecting mechanism 35 can be provided directly to the periphery of the joint shaft 4 of the horizontal arm 3, thereby the necessity of substantially changing a basic structure of the horizontal arm 3 and the vertical arm 1 can be eliminated.

Next, procedures of a balance adjustment in the balancing stand will be described. In an initial state where the stand has been set on a predetermined location, the horizontal arm 3 is in a locked state effected by the electromagnetic clutch 6. In the initial state, the operation microscope 7 is mounted with both the side scope 8 and camera 9, and the whole weight of the operation microscope 7, side scope 8 and camera 9 is greater than that of the counterweight W.

Subsequently, the electromagnetic clutch 6 is energized to release the locked state of the horizontal arm 3 and the latch 7 is protruded beyond the front end of the lever 16 for meshing with the gear 13. When the electromagnetic clutch 6 is disengaged, the front end of the horizontal arm 3 tends to move upward and the rear end thereof tends to move downward because, as described above, the operation microscope 7 and the other weights are heavier than the counterweight W. However, because of the states where the latch 17 of the lever 16 and the gear are meshed with each other and the rear end of the lever 16 abuts against the stopper 18a when the rear end of the lever 16 tends to move downward in response to the angular movement, namely downward movement of the front end of the horizontal arm 3, the lever 16 is prevented from rotating further. Therefore, significant angular movement of the horizontal arm 3 is prevented, thereby such a danger that either the front end or the rear end of the horizontal arm 3 may strike against some apparatus or the like present nearby will be eliminated. Simultaneously, no substantial movement of the horizontal arm 3 can contribute to protection of the operation microscope 7 and the other weights and the horizontal arm itself.

When the upper switch 20a is bushed by the rear end of the lever 16, the switch 20a transmits signals to the motor 12 to displace the counterweight W in a balancing direction (backward). When the displacement of the counterweight W is completed to achieve a balanced condition between the counterweight W and the operation microscope 7 and the other weights, abutment of the rear end of the lever 16 against the stopper 18a is eliminated, thereby the rear end of the lever 16 is assumed in a neutral position in the clearance defined between the above and below stoppers 18a,18b.

Therefore, in this condition, if the latch 17 is retracted into the lever 16 to disengage itself from the gear 13, balance has been already achieved, so that the horizontal arm 3 does not exhibit any angular movement. Therefore, an operator can displace the operation microscope 7 and the other weights to desired positions in height. Angular movement of the horizontal arm 3 will allow the operation microscope 7 and the other weights to stop in desired positions in height in the aerial space even if the operation microscope 7 and the other weights are displaced to any optional positions in height. When the locations of the operation microscope 7 and the other weights are completely determined, the horizontal arm 3 should be locked via the electromagnetic clutch 6 to fix the position of the operation microscope 7 and the other weights for the purpose of observation and taking pictures.

In the above embodiment, exemplification is given where the operation microscope 7 and the other weights are heavier than the counterweight W. In a case where the operation microscope 7 and the other weights are lighter than the counterweight W, the procedures described above should be reversed.

Figure 4:
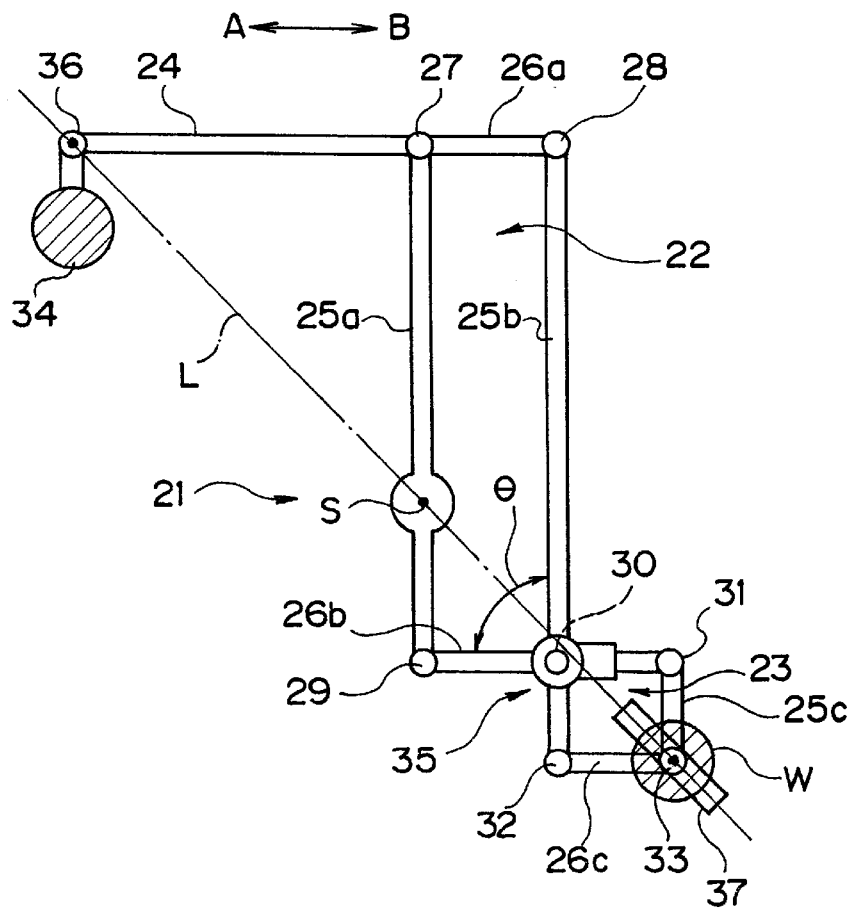
FIG. 4 is a schematic view illustrating a balancing stand according to a second embodiment of the invention.

FIG. 4 illustrates a second embodiment of the invention. In the embodiment, the detecting mechanism 35 appeared in the first embodiment is applied to a parallel linkage mechanism 21 which is formed by a combination of a plurality of vertical arms and horizontal arms.

The parallel linkage mechanism 21 comprises a first parallel linkage 22, a second parallel linkage 23 and a support arm 24. The first parallel linkage 22 and the second parallel linkage 23 are formed by a combination of vertical arms 25a,25b,25c and horizontal arms 26a,26b,26c. The vertical arms and horizontal arms are respectively formed by a set of arms consisting of three arms. Each vertical arm 25a,25b,25c and each horizontal arm 26a,26b,26c respectively intersects in a rotatable manner via one of joint fulcrums 27–33.

The support arm 24 is formed as a forward extension of the upper horizontal arm 26a from the joint shaft 27, and has a weight 34 supported at a front end thereof. The front vertical arm 25a has on a part thereof a fulcrum S at which the entire parallel linkage mechanism 21 is supported on a not-shown base. At a rear end of the second parallel linkage 23, a counterweight W is provided in a moveable manner on a rail 37. A distal end 36 of the support arm 24, the joint fulcrum 33, and a fulcrum S all lie on a straight line L. The parallel linkage mechanism 21 displaces angularly within a range of an angleθ.

Further, a detecting mechanism 35 identical to the counterpart appeared in the above embodiment is provided at the joint fulcrum 30 for both the vertical arm 25b and the horizontal arm 26b. Therefore, the detecting mechanism 35 allows manual balancing adjustment between the weight 34 and the counterweight W. Due to its compactness, the detecting mechanism 35 is easily applicable to an existing balancing stand employing the parallel linkage mechanism 21.

According to the invention, a latch provided at a distal end of a lever is urged to engage with a gear fixed at a joint fulcrum jointing a vertical arm and a horizontal arm, for effecting angular displacement, thereby actuating a switch for a detecting mechanism. Because the mechanism is compact, it is easily applicable to existing balancing stands in which for example a parallel linkage mechanism formed with a combination of a plurality of vertical arms and horizontal arms is supported at a predetermined fulcrum. Signals are transmitted from the actuated switch to a driving mechanism to move the counterweight automatically in a balancing direction for effecting balancing adjustment, so that time as required for an adjustment operation can be reduced and unskilled operators can perform an adjustment operation easily. The detecting mechanism is further provided with a pair of stoppers combined with a lever for preventing the horizontal arm and a parallel linkage mechanism interlocking therewith from moving so substantially beyond abutment of the stoppers against the lever in unbalanced conditions, thereby there is no danger that the horizontal arm may strike against persons or equipment present nearby. Thus, physical engagement between the stoppers and the other end of the lever forcedly prevents the horizontal arm from rotating further in a structural sense. Accordingly, if an electrical failure should happen to the switches or the like, any substantial movement of the horizontal arm caused by unbalance in weight will be completely prevented and with the result of that, the present apparatus is advantageous in an aspect of safety.

What is claimed is:

1. An automatic balancing apparatus for a balancing stand comprising:

a vertical arm and a horizontal arm mounted to a joint fulcrum in a pivotal manner, said joint fulcrum being fixed to either said vertical arm or a horizontal arm;

weights being weighed to an end side of said horizontal arm;

a counterweight for balancing with respect to said weights being weighed to the other end side;

a detecting mechanism for detecting unbalanced conditions of said horizontal arm; and a driving mechanism for displacing said counterweight in a balancing direction in response to signals outputted by said detecting mechanism, wherein said detecting mechanism is provided with: a gear fixed to the joint fulcrum; a lever pivotally supported at a middle portion thereof on said vertical arm or horizontal arm whichever not being integrally fixed to said gear, said lever further provided with at one end thereof a telescopic latch engageable with and detachable from said gear; a pair of stoppers opposed to each other with a predetermined clearance with the other end of said lever being sandwiched between said stoppers; urging means for holding the other end of the lever at a neutral position of said clearance; and a pair of switches provided opposed each other with the other end of the lever interposed therebetween, said switches being pushed by the other end of the lever.

2. An automatic balancing apparatus for a balancing stand according to claim 1, wherein a parallel linkage mechanism formed with a combination of a plurality of vertical linkage arms and horizontal linkage arms is supported at a predetermined fulcrum, and said joint fulcrum has mounted a set of said vertical linkage arm and said horizontal linkage arm of said parallel linkage mechanism.

3. An automatic balancing apparatus for a balancing stand according to claim 1, wherein the weight is an operation microscope.

4. An automatic balancing apparatus for a balancing stand according to claim 2, wherein the weight is an operation microscope.

* * * * *